United States Patent
Baker et al.

(10) Patent No.: US 6,543,181 B1
(45) Date of Patent: Apr. 8, 2003

(54) FRUIT FLY ATTRACTANT COMPOSITIONS

(75) Inventors: Thomas C. Baker, Ames, IA (US);
Junwei Zhu, Ames, IA (US);
Kye-Chung Park, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 09/888,141

(22) Filed: Jun. 22, 2001

(51) Int. Cl.[7] .................. A01M 1/20; A01N 25/00; A61K 31/405
(52) U.S. Cl. ..................... 43/107; 424/84; 514/415
(58) Field of Search .................. 424/84; 43/107; 514/415

(56) References Cited

U.S. PATENT DOCUMENTS

| | | | |
|---|---|---|---|
| 5,008,107 A | 4/1991 | Warner ................... | 424/84 |
| 5,464,626 A | 11/1995 | Warren et al. ............. | 424/408 |
| 5,490,349 A | 2/1996 | Muramatsu ................ | 43/122 |
| 6,106,821 A | 8/2000 | Baker et al. ............... | 424/84 |

OTHER PUBLICATIONS

"Chemical Attractants for the Adult House Fly" Brown and Lockley. J. Econ. Entomology. vol. 54 No. 4, pp. 670–674 (1961).*

"Field Comparisons of Liver and a New Chemical Mixture as Attractants for the Screwworm Fly" Coppedge et al. Environmenta Entomology. vol. 6 No. 1, pp. 66–68 (1977).*

"Swormlure–4: A New Formulation of the Swormlure–2 Mixture as an attractant for Adult Screwworms, *Cochliomyia hominivora* (Diptera: Calliphoridae)" Mackley and Brown. J. Econ. Entomology. vol. 77 No. 5, pp. 1264–1268 (1984).*

"House Flies and Pig Manure Volatiles: Wind Tunnel Behavioral Studies and Electrophysiological Evaluations" Cosse and Baker. J. Agric. Entomol. vol. 13 No. 4, pp. 301–317 (1996).*

"Volatile Components of a Chicken Feather Hydrolysate that is Highly Attractive to the West Indian and Mexican Fruit Fly (Diptera: Tephritidae)" DeMilo et al. J. Entomol. Sci. vol. 32 No. 3, pp. 245–256 (1997).*

Barrows, W.M., "The Reactions of the Pomace Fly, *Drosophila ampelophila* Loew, to Odorous Substances", *The Journal of Experimental Zoology, IV* (*4*), (Oct. 1907), pp. 515–537.

Hutner, S.H., et al., "Chemicals Attracting Drosophila", *The American Naturalist, LXXI* (*737*), (1937), pp. 575–581.

Reed, M.R., "The Olfactory Reactions of *Drosophila melanogaster* Meigen to the Products of Fermenting Banana", *Physiological Zoology, XI* (*3*), (1938), pp. 317–325.

West, A.S., "Chemical Attractants for Adult Drosophila Species", *Journal of Economic Entomology, 54* (*4*), (Aug. 1961), pp. 677–681.

* cited by examiner

Primary Examiner—Mukund J. Shah
Assistant Examiner—Zachary C. Tucker
(74) Attorney, Agent, or Firm—Schwegman, Lundberg, Woessner & Kluth, P.A.

(57) ABSTRACT

A Drosophila fruit fly attractant composition including: a volatile short chain carboxylic acid, a volatile short chain alcohol, a volatile aryl substituted alcohol, and a nitrogen compound. The invention also includes Drosophila fruit fly attractant-trapant compositions.

39 Claims, No Drawings

FRUIT FLY ATTRACTANT COMPOSITIONS

CROSS REFERENCE TO COPENDING APPLICATIONS

Attention is directed to copending patent application U.S. Ser. No. 09/730,486, filed Dec. 5, 2000, entitled "Attractants of Beneficial Insects", which discloses compositions and methods useful for attracting predatory insects.

FIELD OF THE INVENTION

This invention relates to the field of insect attractants and in particular to compositions and methods of use for attracting and trapping Drosophila fruit flies.

BACKGROUND OF THE INVENTION

The genus Drosophila, which includes the well-known pest species *Drosophila melanogaster* (the vinegar fly), as well as many other nuisance species, is seemingly ubiquitous and synonymous with ripe or overly ripe fruit and vegetables. Unlike fruit flies in the family Tephritidae, which are capable of causing extensive crop damage, Drosophila are not agricultural pests. However, Drosophila can be objectionable to consumers or marketers of produce, and often are associated by consumers unsanitary produce or premises.

There is no way to easily and safely use insecticides in food-handling facilities or supermarkets without causing concern for consumers. The fruit flies or the affected fruit or vegetables need to be removed. One potentially effective way to remove Drosophila fruit flies from premises is through the use of feeding or oviposition attractants placed in unobtrusive traps that are selectively deployed in sensitive environments where fruit flies are a problem. However, the only existing commercially available fruit fly trap appears to be only moderately effective in removing Drosophila.

In U.S. Pat. No. 5,490,349, issued Feb. 13, 1996, to Muramatsu, there is disclosed an insect trap which contains a liquid insect attractant which is fully enclosed so that the trap may be shipped without spillage or loss. The trap includes an enclosure which provides a funnel shaped portion terminating in a substantially translucent nipple. The insect trap may be commissioned into service by piercing the nipple thereby creating an inlet into the interior chamber through which insects will be drawn by the liquid attractant. The nipple is formed by a thermal process so that the walls of the inlet are drawn thin creating translucent walls which form a bright spot of light larger than the inlet's opening, thereby making it difficult for trapped insects to find the opening and gain freedom. Except for the terminal portions of the inlet, the enclosure is substantially opaque so that the contents of the insect trap are not visible to the public.

There exists a commercial product that is believed to be an embodiment of the above U.S. Pat. No. 5,490,349, which consists of a small plastic vessel-type trap with a small hole in the top, and named "Natural Catch® Plus Fruit Fly Trap". The liquid attractant used in the trap is believed to be primarily vinegar, which is referred to hereinafter as "Anderson's solution."

In U.S. Pat. No. 5,464,626, issued Nov. 7, 1995, to W. Warren, et al., there is disclosed a method for attracting the insect species *Culex nigripalpus, Aedes atlanticus, Culex salinarius, Aedes vexans*, Culex spp., Simulium spp., *Psorofeta ferox, Aedes infirmatus, Drosophila melanogaster*, Coccinellidae, *Anopheles crucians, Psoroferia columbiae*, Culicoides spp. and Aedes spp., using a compound having a dimethyl substituted oxymethyl cyclohexane derivative structure. This attractant finds utility primarily as a bait enhancer for acute toxins and/or trapping devices.

In U.S. Pat. No. 5,008,107, issued Apr. 16, 1991, to C. Warren, et al., there is disclosed a novel attractant composition for use with synanthropic flies (the so-called 'filth flies' such as the house fly) which includes indole and skatole, a pheromone, trimethylamine hydrochloride, and a suitable carrier.

In U.S. Pat. No. 6,06,821, issued Aug. 22, 2000, to Baker et al., there is disclosed (house) fly attractant compositions that comprise at least one volatile short chain carboxylic acid, at least one organic sulfide, and at least one nitrogen heterocycle. In a preferred embodiment the composition additionally comprises at least one ammonia-releasing compound. In a particularly preferred example, the composition is preparable by combining, for example, the carboxylic acid, the organic sulfide and the nitrogen heterocycle. The invention also relates to an insect trap comprising a means for retaining flies and an insect attractant composition of this invention. The trap is useful in commercial, residential and livestock facilities.

Other references related to attracting Drosophila include: West, A. S. (1961). Chemical attractants for adult Drosophila species. J. Econ. Entomol. 54:677–681; Hutner, S. H., Kaplan, H. M., and Enzmann, E. V. 1937. Chemicals attracting Drosophila. Amer. Nat. 71:575–581; Reed, M. R. 1938. The olfactory reactions of *Drosophila melanogaster* Meigen to the products of fermenting bananas. Physiol. Zool. 11:317–325; and Barrows, W. M. 1907. Reaction of the pomace fly, *Drosophila ampelophila* Loew, to odorous substances. J. Exp. Zool. 70: 515–537.

For Drosophila fruit flies, new chemical attractant compositions are needed to create attractant-traps that will be more effective at reducing the presence of Drosophila fruit fly adults. Although much work has been done on defining attractants for flies in the families Muscidae and Tephritidae, relatively little has been done to define compositions that are highly attractive to flies in the unrelated family Drosophilidae, which includes flies in the genus Drosophila.

SUMMARY OF THE INVENTION

This invention relates to Drosophila fruit fly attractant and attractant-trapant compositions, to fruit fly traps which include the fruit fly attractant and attractant-trapant compositions, and to methods for attracting and trapping fruit flies using the compositions of this invention.

Particularly effective attractants for fruit flies appear to be natural products. Especially effective fruit fly attractants are the volatile natural products of the ripening and decaying of fruit or vegetable produce which can signal and serve as sites for fruit fly feeding and oviposition. The present invention identified the compounds emanating from ripe and decaying fruit, and further identified those compounds which had the greatest ability to attract Drosophila fruit flies to traps. Certain of the identified compounds were selected for use in attractant-trapant formulations and fruit fly trap applications based on neurophysiological activity on olfactory neurons on the antenna, coupled with trapping experiments with Drosophila melanogaster fruit flies.

The present invention provides in embodiments, for example:

A Drosophila fruit fly attractant composition comprising: a volatile short chain carboxylic acid, a volatile short chain alcohol, a volatile aryl substituted alcohol, and a nitrogen compound;

A synthetic fruit fly attractant-trapant composition comprising:
from about 10 to about 300 parts by weight acetic acid,
from about 0.1 to about 30 parts by weight ethanol,
from about 0.1 to about 100 parts by weight 2-phenyl ethanol,
from about 0.1 to about 100 parts by weight of a nitrogen compound,
and from about 10 to about 1,000 parts by weight a sugar, and
from about 10 to about 1,000 parts by weight water; and A kit useful for attracting and trapping fruit flies comprising:
a bait in accordance with the compositions illustrated herein and in an amount effective to attract Drosophila fruit flies, and
a housing adapted for containing the bait and for retaining the attracted Drosophila fruit flies;

A method for attracting Drosophila fruit flies comprising: positioning in a fruit fly area an effective amount of a fruit fly attractant composition of the present invention; and A synthetic Drosophila fruit fly attractant composition prepared by combining an effective amount of a simple sugar; a volatile carboxylic acid; a short alkyl chain alcohol; an aryl substituted short alkyl chain alcohol; and at least one nitrogen heterocycle compound, wherein the composition attracts a substantial majority of available Drosophila melanogaster fruit flies and in preference to ripe or rotten fruit, or produce, that is situated in close proximity to the synthetic fruit fly attractant.

In a preferred embodiment of the method, the above mentioned positioning takes place in, for example, in a residence, or in a commercial facility, including, but not limited to a cafeteria, a restaurant, a grocery produce section, a produce packing, distribution or staging area, a school, a hospital, or any other areas perceived to be infested with, or at risk to be infested with, Drosophila fruit flies. The present invention is of interest to those who are or use professional pest-control services because the compositions and methods can be, if desired, but not limited to natural ingredients or synthetic equivalent compounds which materials have exceedingly low toxicity in humans or animals. The present invention can also, if desired, be practiced without the use of potentially harmful insecticides.

In addition, the fruit fly attractant or attractant-trapant compositions of the invention can further comprise, in embodiments, at least one additional component, such as, volatile ester compounds, such as volatile aromatic esters or acetic acid esters, which compounds can be added to the mixture in measured amounts or can be generated in situ by, for example, controlled or spontaneous esterification.

In another preferred embodiment the fruit fly attractant composition can additionally include an insecticide.

These and other features of the present invention are illustrated herein.

Definitions

The following definitions are used, unless otherwise described.

"Attractant" refers to any composition, chemical or other stimuli that causes, either directly or indirectly, an insect to displace toward the source of the stimuli. Attractants include thermostimuli, mechanostimuli, for example, airborne sound waves, or substrate borne pressure waves, electromagnetic stimuli including visual stimuli such as patterns, objects, color, light, and chemical stimuli including odors. A chemical attractant can be an individual compound or a composition, including more than one compound, that either directly or indirectly, such as into the wind, causes the insect to displace toward the source of the stimuli.

"Trapant" refers to any composition, chemical or other stimuli that causes a target insect to enter, dwell, linger, or remain nearby or within a trap device. Glues or adhesive compounds or compositions are examples of known and effective trapants. Glues and the like trapant materials or adjuvants can be disadvantaged, for example, in processing and handling properties, they can plug or foul trap components or access apertures, or they can have anti-linger, anti-feedant, or other fruit fly deterrent or repellent properties, such as the presence of minor or even trace amounts of organic solvents.

"Attractant-Trapant" refers to any compound(s) or composition(s) which possess a combination of attractant and trapant qualities.

"Fugitive" refers to any formulated or in situ generated component or components which can be, for example, volatile, likely to evaporate, deteriorate, change, fade, disappear, or the like concentration diminutive processes. For certain in situ generated fugitive components, such as 2-phenylethyl acetate or ethylacetate of the present invention, the concentration at any time may vary over a wide range, for example, a concentration of about 0 to less than about 10 ppm when the attractant or attractant-trapant composition is prepared and which concentrations can decrease or increase with time followed by a period of continuous decrease in concentration by, for example, continued evaporation.

"Naturally occurring" refers to compounds used to prepare the compositions of the present invention that are known to be found in or emitted by, for instance, ripe or decaying fruit, vegetables, and the like other organic matter.

"Volatile" refers to compounds, compositions, or mixtures with a sufficient vapor pressure so that at least some of the matter can be readily vaporized at ambient temperature or temperatures slightly above ambient, and the resulting vapors can be detected and responded to by, for example, the living fruit fly, the fruit fly's extirpated antenna, or the airborne effluent from sources of these compounds can be adsorbed onto solid surfaces and concentrated, and then detected and analyzed by gas chromatographic or related analytic means, such as GC/MS.

The indefinite articles "a" and "an" mean "at least one" or "one or more" when used in this application, including the claims, unless specifically indicated otherwise.

DETAILED DESCRIPTION OF THE INVENTION

This invention relates to compositions which possess either or both attractant and trapant properties for use in control of Drosophila fruit flies such as Drosophila melanogaster. The attractant or trapant compositions of the present invention are prepared from chemicals that were identified, for example, from natural sources, such as, from decaying fruit. In addition, the compositions of this invention include chemicals with properties similar to those of the compounds identified in fruit or produce that also have fruit fly attractant properties including electroantennogram-stimulating activity and the ability to stimulate upwind flight activity in a wind tunnel bioassay, as described herein.

The present invention, in embodiments, provides a synthetic fruit fly attractant composition comprising:
- a volatile short chain carboxylic acid,
- a volatile short chain alcohol,
- a volatile aryl substituted alcohol, and
- a nitrogen compound.

These compositions can further comprise water, preferably deionized water. Most of the other components of the composition are soluble or miscible with the water. The water can act as a useful formulation vehicle or carrier liquid which provides added formulation flexibility and latitude, for example, in preparing and administering concentration specific or concentration adjusted formulations for use in a variety of applications and conditions. Although not wanting to be limited by theory, it is believed that the water, while not believed to an essential component of the attractant composition, provides desired humidity characteristics in and around the composition when used in attractant or attractant-trapping applications and it is further believed that the water component may enhance the attractant and trapant properties of the compositions of the present invention, for example, the water or its concomitant humidity may act as a lingerant, which lingerant by definition encourages the attracted fruit flies to linger longer than the flies would with comparable formulations but without the water or humidity.

The compositions of the present invention can further comprise a sugar compound. The sugar is preferably a naturally occurring and low molecular weight saccharide. A preferred sugar or saccharide is, for example, sucrose. Other sugar compounds can include other known natural or synthetic sugar compounds such as fructose, glucose, and the like sugar compounds. Other sugar compounds can include sugar-like compounds such as artificial sweetener compounds, for example, saccharin, aspartame, and the like compounds. Although not wanting to be limited by theory, when water is used with the attractant composition, the sugar compound increases the capture of Drosophila fruit flies, but whether it contributes to increased attraction from a distance is less certain. The sugar, like the abovementioned water component, may be an important or contributing factor in enhancing the effectiveness of the compositions of the present invention, for example, improving the trapant properties of the composition.

The compositions of the present invention can further comprise either or both ethylacetate and 2-phenyl ethylacetate. Either or both the ethylacetate and 2-phenyl ethylacetate can be added as separate components and in measured amounts to form the composition. Additionally or alternatively, and depending upon the other components present, the relative amounts of other components present, or the conditions under which the composition is formulated or stored, such as with or without water present, evaporation, extent of sugar hydrolysis, bacterial contamination, ambient or heated mixing, duration of storage, and the like considerations, either or both the ethylacetate and 2-phenylethylacetate can be generated in situ, for example, by esterification of an alcohol and an acid component originally present or generated in situ in the mixture of ingredients combined to form the composition. The in situ generated ethylacetate and 2-phenyl ethylacetate can arise, for example, from esterification of acetic acid and ethanol and 2-phenyl ethanol (phenethyl alcohol), respectively. The in situ generated ethylacetate and 2-phenyl ethylacetate can be present, for example, in the volatiles emanating from the attractant composition, such as, in trace amounts to minor amounts of, for example, from less than about 0.1 percent to greater than about 99 percent relative to the amounts of the respective precursor alcohols present in the airborne emissions, or alternatively, by weight based on the total weight of the initially formulated composition. When the ethylacetate and 2-phenyl ethylacetate are deliberately, initially added as formulation components they can be present in amounts of from about 0.01 parts by weight to greater than about 10 parts by weight based on the total weight of the composition. Whether the ester compounds are added separately or generated in situ, they are considerably less hydrogen bonding and less hydrophilic compared to the corresponding acid compound forms and possess properties consistent with the abovementioned "fugitive" compounds, such as, having a potentially variable or changing concentration profile with time.

In embodiments the volatile short chain carboxylic acid can be, for example, acetic acid and can be present, for example, in an amount of from about 60 to about 70 parts by weight. Volatile short chain carboxylic acids include carboxylic acids having 1–8 carbon atoms and preferred short chain carboxylic acids include those carboxylic acids having 2–5 carbon atoms. Preferably the carboxylic acids used in the composition of this invention are those that are naturally occurring volatiles present in fruit, particularly acetic acid. These include formic acid, acetic acid, lactic acid, propanoic acid, butanoic acid, 2-methylpropanoic acid, pentanoic acid, 3-methylbutanoic acid, 2-methylbutanoic acid, 2-methyl-2-butanoic acid, hexanoic acid, 4-methylpentanoic acid, 2-methylpentanoic acid, heptanoic acid, octanoic acid, benzoic acid, phenylethanoic acid, and 3-phenylpropanoic acid. Also, in a preferred embodiment the volatile short chain carboxylic acids can be either straight or methyl branched aliphatic carboxylic acids. Preferred carboxylic acids include for example, acetic acid, propanoic acid and butanoic acid. The volatile short chain alcohol can be, for example, ethanol and can be present in an amount of from about 1 to about 10 parts by weight. Other suitable alcohols include, for example, methanol, isopropanol, propanol, butanol, pentanol, hexanol, and cis-3-hexanol.

The aryl substituted alcohol can be, for example, 2-phenyl ethanol and can be present in an amount of from about 1 to about 30 weight percent. Other suitable aryl substituted alcohols include, for example, phenyl methanol and 2-phenyl propanol.

The nitrogen compound or nitrogen heterocycle compound can be, for example, indole, 3-methyl-1H-indole also known as skatole, and can be present in an amount of from about 0.003 to about 1.0 parts by weight. The trialkylamine compound can be, for example, trimethylamine hydrochloride and the like compounds and salts thereof, and can be present in an amount of from about 0.01 to about 0.1 parts by weight. In embodiments the trialkyl amine compound if selected can have from 3 to 9 carbon atoms. The trialkyl amine can be, for example, triethylamine or preferably trimethylamine.

The attractant and attractant-trapant compositions of the present invention can also include one or more terpenoid compounds. The terpenoid compound can be, for example, alpha-copaene, a tricyclic sesquiterpene, and can be present in an amount of from about 0.1 to about 10 parts by weight of the composition. Other suitable terpenoid compounds include, for example, alpha-pinene, beta-pinene, beta-myrcene, alpha-terpinene, linalool, carene, trans-beta-caryophyllene, limonene, beta-selinene, and the like compounds and mixtures thereof.

The present invention provides, in embodiments, a Drosophila fruit fly attractant-trapant composition comprising:

from about 10 to about 300 parts by weight acetic acid, from about 1 to about 30 parts by weight ethanol, and from about 0.1 to about 100 parts by weight 2-phenyl ethanol, and from about 0.001 to about 1.0 parts by weight of nitrogen compound, for example, a nitrogen heterocycle such as indole or skatole, or alternatively, about 0.05 parts by weight of trialkylamine compound such as trimethylamine(HCl).

Other optional components can include, for example, about 10 to about 1,000 parts by weight of a water, about 10 to about 1,000 parts by weight of a sugar, from about 0.1 to about 30 parts by weight ethyl acetate, from about 0.1 to about 100 parts by weight 2-phenethyl acetate, from about 0.1 to about 100 parts by weight of a terpenoid compound such as alpha-copaene, or mixtures thereof.

The present invention provides, in embodiments, a fruit fly attractant-trapant composition comprising:

from about 30 to about 100 parts by weight acetic acid, from about 1 to about 10 parts by weight ethanol, from about 1.0 to about 30 parts by weight 2-phenyl ethanol, and from about 0.01 to about 1.0 parts by weight of a nitrogen compound.

Optional additives can include, for example, about 10 to about 1,000 parts by weight of a water, about 10 to about 1,000 parts by weight of a sugar, from about 0.3 to about 10 parts by weight 2-phenethyl acetate, from about 0.3 to about 3 parts by weight ethyl acetate, from about 0.01 to about 0.1 parts by weight of trimethylamine HCl in admixture with the nitrogen compound, such as, the above mentioned nitrogen heterocycle or in lieu of the nitrogen compound, and from about 1.0 to about 10 parts by weight a terpenoid compound such as alpha-copaene, or mixtures thereof.

The present invention provides, in embodiments, a fruit fly attractant-trapant composition comprising:

from about 65 to about 70 parts by weight acetic acid, from about 2 to about 4 parts by weight ethanol, from about 9 to about 11 parts by weight 2-phenyl ethanol, and from about 0.01 to about 0.5 parts by weight of a nitrogen compound.

Optional additives can include, for example, about 10 to about 1,000 parts by weight of a water, about 10 to about 1,000 parts by weight of a sugar, from about 0.1 to about 9.0 parts by weight 2-phenethyl acetate, from about 0.02 to about 0.4 parts by weight ethyl acetate, from about 0.01 to about 0.1 parts by weight of trimethylamine HCl in admixture with the nitrogen compound, such as, the above mentioned nitrogen heterocycle or in lieu of the nitrogen compound, and from about 1.0 to about 10 parts by weight a terpenoid compound such as alpha-copaene, or mixtures thereof.

In an exemplary embodiment the present invention provides a fruit fly attractant-trapant composition comprising:

about 67 parts by weight acetic acid, about 3 parts by weight ethanol, about 10 parts by weight 2-phenyl ethanol, and about 0.3 parts by weight of nitrogen containing compound or nitrogen heterocycle, such as indole or skatole. Other optional components can include, for example, mixtures of water and a sugar, for example, in amounts of from about 10 to about 1,000 parts by weight of a water and about 10 to about 1,000 parts by weight of a sugar. Other optional components can include, for example, about 1 part by weight 2-phenethyl acetate, about 0.3 parts by weight ethyl acetate, about 0.05 parts by weight of trialkylamine compound such as trimethylamine(HCl), about 5 parts by weight of a terpenoid compound such as alpha-copaene, or mixtures thereof. The nitrogen compound or nitrogen heterocycle compound can be, for example, indole, 3-methyl-1H-indole, or a trialkylamine or a salt thereof with from 3 to about 12 carbon atoms, and mixtures thereof. Examples of the trialkylamine compound include trimethylamine, triethylamine, and salts thereof. The trialkylamine salts can include but are not limited to, for example, hydrogen halides, such as, hydrochloride salts, carbonates, acetates, benzoates, tosylates, and the like salts.

The volatile short chain carboxylic acid can be, for example, synthetic equivalents of those short chain carboxylic acids that are found in fresh or fermenting fruit, including straight or methyl-branched aliphatic carboxylic acids containing from 2 to 5 carbon atoms, such as acetic acid, propanoic acid, butyric acid, and the like compounds and mixtures thereof. The nitrogen compound similarly is preferably a synthetic equivalent to those nitrogen compounds that are naturally found in fresh or fermenting fruit.

Although not wanting to be limited by theory the compositions of the present invention are believed to be effective as attractant-trapant compositions because they have properties which mimic or approximate either or both a fruit fly feedant stimulant and a fruit fly lingerant stimulant, that is, a fruit fly once attracted to the situs or source of the composition, such as, in an open or closed bait containing trap the flies may have a tendency to linger longer than they might otherwise be expected to, for example, compared to a control composition which is neither an attractant or a trapant composition.

The composition can further comprise an insecticide. Suitable insecticides are preferably include those insecticides which have high Drosophila fruit fly kill rates but which insecticides have physical properties which are generally not objectionable to the target fruit fly pests, for example, where objectionable properties of the insecticide might negatively impact or impair the excellent attractant or trapant properties of the compositions.

In use or situational trapping applications, the attractant-trapant composition can be contained, for example, in a sustained release dispenser. Preferably, the Drosophila fruit fly attractant or attractant-trapant composition in the trap is provided, for example, as a free aqueous solution also serving as a trapant, or in a sustained release matrix. The sustained release matrix or dispenser can include, for example, a hollow capillary fiber, a polyethylene or polypropylene tube through which the attractant composition volatilizes, a piece of cotton, rubber, leather, plastic, glass or fiberglass, or wood or wood-products impregnated with the attractant composition, a gel or paste, a membrane enveloping the attractant composition, or a pump that dispenses amounts of the attractant composition out of an internal reservoir at a metered rate or like embodiments.

The compositions of the present invention are capable of stimulating a volatile plume-oriented upwind flight of a fruit fly in a wind tunnel having a wind velocity of, for example, about 50 cm per second. The compositions can also stimulate an electroantennogram response from a Drosophila fruit fly antenna, and which responses are consistent and concurrent with major components emitted from, for example, ripe or decaying fruit.

The present invention provides, in embodiments, a Drosophila fruit fly attractant-trapant composition comprising:
- from about 50 to about 100 parts by weight acetic acid,
- from about 1 to about 10 parts by weight ethanol,
- from about 1 to about 20 parts by weight 2-phenyl ethanol,
- from about 0.1 to about 1.0 parts by weight of a nitrogen compound,
- from about 10 to about 1,000 parts by weight a sugar, and
- from about 10 to about 1,000 parts by weight water.

The nitrogen compound can be, for example, indole, skatole, or trimethylamine. The sugar can be, for example, sucrose, glucose, fructose, and the like sugars alone, or mixtures thereof. The sugar component such as sucrose can be, for example, in the anhydrous form prepared by heating, or a water hydrate or absorbate form which forms typically contains about 1 weight percent of water. When the hydrate form is selected the relative ratio or concentration of the attractant composition ingredients can be adjusted accordingly. Although not wanting to be limited by theory it is known that sucrose is readily hydrolyzed in dilute acid, partially or completely, to a mixture of its component monosaccharides, glucose and fructose. It is also well known that sucrose is highly soluble in water, and has slight solubility in alcohol, such as ethanol. It is also known that sucrose is fermentable but resists bacterial decomposition at high concentrations by presumably creating inhospitable concentration gradients. Thus the compositions of the present invention can be formulated with or preferably without added preservative compounds which might assist or compromise the attractant or trapant properties of the composition. Although not wanting to be limited by theory the attractant or attractant-trapant compositions formulated with sucrose in amounts, for example, above about 50 weight percent based on the total weight of the composition are believed to be self-preserving, that is, the compositions can be formulated free of added preservatives against bacterial degradation. Alternatively, it is known that sucrose fermentation products can include ethanol, acetic acid, formic acid, and related oxidation products, and which products may further contribute or enhance the attractant or trapant properties of the composition by, for example, increasing the level of the aforementioned fugitive ester compounds or may themselves be fugitive compounds. Thus in embodiments of the present invention, for example, when the attractant-trapant compositions are formulated for use at lower concentrations or more dilute concentrations and without a preservative, there may occur sucrose oxidative degradation which consequently produces a relative increase in volatile components as a result of the diminution of the sucrose component and its reapportionment as, for example, volatile alcohols, acids, or as esterification products.

Although not wanting to be limited by theory the water and sugar are believed to be non-essential to the attractant composition and its effectiveness as a fruit fly attractant. However, the water and sugar may be important or essential to the effectiveness of the composition as a trapant composition.

The present invention provides, in embodiments, a synthetic fruit fly attractant composition prepared by combining:
- acetic acid,
- ethanol,
- 2-phenyl ethanol,
- and a nitrogen compound of indole, skatole, trimethylamine, or mixtures thereof.

The attractant compositions, attractant-trapant compositions and the preparative processes can further comprise combining with the above mentioned ingredients, for example, sucrose, glucose, fructose, water, 2-phenyl ethyl acetate, ethyl acetate, or mixtures thereof.

The present invention provides, in embodiments, a kit useful for attracting and trapping Drosophila fruit flies comprising:
- a bait with, for example, any of the above or below mentioned synthetic fruit fly compositions in an amount effective to attract fruit flies, and
- a structure, such as a housing or support surface, adapted for containing the bait and adapted for retaining the attracted Drosophila fruit flies.

The present invention provides a Drosophila fruit fly trap comprising a structure, such as a housing or support surface, to retain Drosophila fruit flies within the trap and any of the above mentioned synthetic fruit fly attractant-trapant compositions. The trap can be, for example, a surface or structure for placing or locating the bait, such as a tape, a housing, or a dish, and can include, for example, a tacky surface, an insecticide, a natural or synthetic pheromone, a one-way "trap box", an electrocution means such as a restricted access electrode, a liquid reservoir, a sponge, a porous solid, and the like surfaces or structures, and combinations thereof. The trap can further comprise if desired, for example, a heat stimuli, a visual stimuli, and the like stimuli, or combinations thereof.

The present invention provides, in embodiments, a method for attracting Drosophila fruit flies comprising:
positioning in a fruit fly area an effective amount of a fruit fly attracting composition comprising:
- from about 50 to about 100 parts by weight acetic acid,
- from about 1 to about 10 parts by weight ethanol,
- from about 1 to about 20 parts by weight 2-phenyl ethanol,
- from about 0.1 to about 1.0 parts by weight of a nitrogen compound,
- from about 10 to about 1,000 parts by weight a sugar, and
- from about 10 to about 1,000 parts by weight water.

The methods of the present invention can further comprise incorporating the above mentioned compositions as part of a trap for collecting the attracted flies. The "fruit fly area" can include, for example, any area or areas that currently have or have been exposed to fresh, frozen, processed, ripe, overly ripe, rotting, or the like fruit or produce and which areas are attractive or conducive to visitation or infestation by Drosophila fruit flies. The "fruit fly area" can include, for example, a residence, a restaurant or cafeteria, a fruit orchard or grove, a winery, a commercial facility such as a fruit or produce processing, packaging, handling, disposal, and the like facilities, a fruit or produce transport container such as a truck, boat, plane, or the like containers, or plant equipment such as juicer.

The present invention provides, in embodiments, a Drosophila fruit fly attractant composition prepared by combining an effective amount of a simple sugar; a volatile carboxylic acid; a short alkyl chain alcohol; an aryl substituted short alkyl chain alcohol; and at least one nitrogen heterocycle compound, wherein the composition attracts a substantial majority of available Drosophila fruit flies and in preference to ripe or rotten fruit or produce situated in close proximity to the synthetic fruit fly attractant. The preference for the composition by the substantial majority of the Drosophilia fruit flies can be, for example, an attraction level of from about 50 to about 60 percent of available feeding fruit flies in an 8-hour period compared to from about 5 percent to about 10 percent of available feeding fruit flies for a competing bait such as a ripe mango.

The identity of the sugar, the acid, the short alkyl chain alcohol, and the aryl substituted short alkyl chain alcohol are, for example, as defined above. The nitrogen heterocycle compound can be, for example, indole, 3-methyl-1H-indole, or mixtures thereof. Exemplary nitrogen heterocycles of this invention include, but are not limited to, for example, indole, skatole (3-methylindole), pyridine, 3-aminopyridine, (2)-methylpyrazine, methylpyrazine, trimethylpyrazine and tetramethylpyrazine. Preferred nitrogen heterocycle-containing compounds include, but are not limited to indole and 3-methyl indole. Other amines such as the aforementioned trialkylamines, and for example diamine compounds, such as 1,4-diaminobutane (putrescine), 1,5-pentanediamine (cadaverine), and the like diamines, can also be used as the nitrogen compound, for example, individually or in various combinations with the above mentioned nitrogen compounds.

Other optional compounds that can be added to the compositions of the present invention, if desired, can include trimethylamine and other amines including, but not limited to methylamine, triethylamine, aminoethane, and the like. Additional optional compounds that can be added to the compositions of the present invention, if desired, can include ethyl acetate and other short-chain alkyl acetates; 2-phenylethylacetate and other short-chain aryl-substituted acetates, including, but not limited to, for example, phenylmethylacetate; alpha-copaene and other terpenoid compounds including, but not limited to, for example, alpha-pinene, beta-pinene, beta-myrcene, alpha-terpinene, linalool, carene, trans-beta-caryophyllene, limonene, methyl salicylate, and beta-selinene.

A method of identifying the preferred compositions of this invention is where fruit volatiles were initially analyzed by coupled gas chromatographic-electroantennographic (GC-EAG) and coupled GC-mass spectrometry (GC-MS) assays to isolate and identify those compounds in the headspace of fruit that are biologically active. The GC-EAG system was used to separate compounds emitted from a natural fruit fly attractant, shown in preliminary experiments to attract and capture large numbers of flies, for example, ripe mango, old grapes, dried grapes, raisins, plum, strawberry, pear, and the like fruits, and the natural attractant and components of the attractant were analyzed for their neurophysiological-stimulating activity. The GC-EAG coupled GC-MS system separates compounds emitted from the natural material while neurophysiologically assessing the compounds for their activity on the fruit fly antenna. The degree of neuronal activity registered on an insect antenna through EAG is strongly correlated with behavior activity (Cosse et al. 1994, J. Chem. Ecol. 21:1823–1836 and Cosse et al. 1995, Entomol. Exp. Appl. 72:233–238). The same array of volatile compounds from the natural material was injected onto a coupled gas chromatographic/mass spectrometric system (GC-MS) to identify the EAG-active volatile compounds. Preferred methods for assessing the volatiles in fruit are provided in Example I and preferred methods for performing GC-EAG are provided in Example II.

The GC-EAG analyses demonstrated that fruit fly antennae selectively responded to a number of compounds that were present in the headspace of fruit, see Table 1 of Example 2. These compounds have been identified in, for example, the headspace volatiles of ripe mango, strawberry, and banana fruit.

Attraction-trapant assays were used to verify the attractant-trapant activity of the identified neurophysiologically active fruit volatiles and permitted testing of various other compositions and optimization of the compositions by testing a variety of ratios of the compounds forming the attractant compositions of this invention. In these studies, fruit flies housed in large screened cages were required to actively fly toward, land on, and enter a small jelly-cup trap having a single ⅛-inch hole in the lid for entry of the flies. Attraction-trapant assays are provided in Example III. In one example, the attraction-trapant assays identified at least two mixtures, one composition comprising seven EAG-active compounds of 2-phenyl ethanol, benzyl acetate, ethyl benzoate, 2-phenylethyl acetate, ethyl phenylacetate, ethyl salicylate, and ethyl cinnamate, and a second composition comprising ethanol, acetic acid, and 2-phenyl ethanol as compositions capable of attracting and trapping fruit flies at a rate similar to that of the known fruit fly attractants containing, for example, malt extract, reference the above mentioned West publication, and also decaying fruit. The trapant-attractancy of any one individual EAG-active compound tested was not much greater than that of the control; however, the combined effect of the compounds as a composition generated highly significant attractant-trapant activity.

Synthetic samples of the compounds of the present invention can be tested as candidate synthetic attractant-trapant compositions using any of a variety of assays such as the trapping methods as provided in Example III. Various blends, ratios, and dosages of the compounds can be tested to identify a combination of compounds that would provide optimal trapant-attractancy of the fruit flies. Similarly, individual compounds can be tested at various dosages for their individual effects in stimulating fruit fly antennae or in stimulating upwind flight activity in the attractant-trapant bioassay and based on results of those studies of individual compounds, selected compounds can be used alone or in combination with other positively identified compounds.

Based on the wind tunnel tests, further testing was performed to determine whether a blend of fewer components could be used as provided in Example IV, Table 3–6. Results from these experiments demonstrated that blends containing only 2-phenyl ethanol and acetic acid, or 2-phenyl ethanol, acetic acid, and ethanol, were good attractants. The ratios of the components of the latter blend were shown to be important in optimizing attractant-trapant activity, and Table 4 of Example IV shows that the ratio of acetic acid to 2-phenyl ethanol is important to the invention in this regard.

This invention also contemplates the use of an aqueous solution of the attractant-trapant blend, with the addition of a sugar as an effective enhancer of trapant-attraction. Table 5 of Example IV shows that the trapant-attractancy of the blend of ethanol, acetic acid, and 2-phenyl ethanol is significantly increased when the blend is put into a 50% sucrose solution in water. Moreover, Table 6 of Example IV shows the increase in trapant-attractancy of the sucrose added to the water in this formulation compared with water lacking the sucrose. Table 14 of Example IV illustrates that sucrose water alone exhibits some attractant-trapant activity.

The activity of 2-phenyl ethanol as a key constituent of the invention is illustrated in Table 7 of Example IV, where omitting the 2-phenyl ethanol from the blend of Table 5, Example IV causes trapant-attractancy to be significantly reduced.

Tables 8–10 of Example IV show that the a blend of 2-phenyl ethanol, acetic acid, and ethanol in sucrose water solution, with either indole, 3-methylindole, or trimethyl amine HCl added, were significantly better attractants. Table 11 of Example IV., shows that such blends with lower proportions of indole added have greater attractant-trapant activity than when higher proportions of indole are used.

The invention contemplates that addition of various additional synthetic volatile components representing those emanating from natural sources attractive to fruit flies may further enhance the attraction-trapant activity of the composition, such as those that were isolated and identified from the headspace of ripe and decaying fruit, see for example Example II above. Table 12 illustrates that the addition of a terpenoid, alpha-copaene, to the composition increases its attraction-trapant activity.

The invention also contemplates the generation of fugitive compounds by, esterification reactions of the short-chain acid and alcohols in the composition, for instance between acetic acid and ethanol, and between acetic acid and 2-phenyl ethanol. These fugitive compounds were detected in airborne emissions from the synthetic blends, as analyzed using the methods in Examples I and II. An example of the ability of fugitive compounds to enhance attractant-trapant activity is shown in Table 13 and 14 of Example IV in which the proportion of one of these reaction products, ethyl acetate, is augmented by the addition of more ethyl acetate to the blend, and the new blend has greater attractant-trapant activity than the blend lacking the additional ethyl acetate. Similarly, augmenting the proportion of 2-phenylethyl acetate in the blend increases trapant-attractancy, as shown in Table 15 of Example IV.

These compositions act as general attractants for, for example, feeding or oviposition, and not as, for example, a sex pheromone, as indicated by the nearly equal sex ratios of the flies captured, shown in Table 16 of Example IV. Furthermore, in none of the examples described above were the accumulated, captured flies themselves influencing the attractant-trapant activity, as shown in Table 17 of Example IV, in which 50 live fruit flies had no better attractant-trapant activity than did a sucrose-water mixture without the live fruit flies.

Example V also provides several preferred methods for testing the attractants of this invention. As a comparison of the efficacy of the present invention, ripe mango fruit was used as the attractant-trapant source in one set of traps, while a blend of preferred constituents 67 parts by weight acetic acid, 3 parts ethanol, and 10 parts 2-phenyl ethanol in an aqueous sucrose solution comprised of 1,000 parts water and 300 parts sucrose was the attractant-trapant in another set of traps. The synthetic blend of the invention attracted and trapped 10 times as many Drosophila fruit flies as the ripe mango fruit, as shown in Table 18 of Example IV. Moreover, Table 19 of Example IV shows that the above blend of the invention captured over 50% of the released flies when in the presence of ripe mango fruit placed around the attractant-trapant source, and that the percentage of flies sitting and feeding on the fruit comprised only 3% of the number captured in the attractant-trapant source.

Comparative experiments were performed using the compositions of this invention employing identical traps, without bait and adding, in one example, the above 3 preferred constituents in aqueous sucrose solution to one set of traps, and in another set of traps adding the liquid attractant portion of the commercial product, Natural Catch Plus®, 'Anderson's Solution'. Table 20 of Example V show that the compositions of the invention attracted and captured significantly more Drosophila fruit flies than those containing Anderson's solution.

The compositions can be incorporated into traps for use inside or outside the home, in commercial facilities including restaurants, health care facilities, and animal care facilities. The invention can be used in a preferred embodiment to attract fruit flies, such as, in a commercial, wholesale, retail, or residential setting. The compositions of this invention can be combined with other stimuli to increase the attractancy of the composition, the potency of a fruit fly attractant, and the overall efficiency of an insect trap containing the composition of this invention. The composition of this invention can be used with one or more other stimuli such as heat stimuli, light stimuli, color or pattern stimuli, and in combination with other chemical stimuli such as pheromones, other attractants and the like. A variety of other food stuffs and compounds are known to attract fruit flies including malt extract and vinegar. These products or volatiles from these products can optionally be included in the composition of this invention. Acceptable levels of attractancy refers to the relative number of fruit flies attracted to the attractant composition that attributes to the total or partial clearing of fruit flies from a particular locale. An acceptable level of attractancy will vary based on the environment where the trap is positioned. For example, an acceptable level of attractancy in a fruit packing facility may be much different from an acceptable level of attractancy in a residence.

Adjuvants are known in the arts of insect attractants and pesticide formulation chemistry, and may serve to extend field longevity or as spreader-stickers, for example, including various petroleum oils such as mineral oil, and various vegetable oils. Further, other agents can be added to augment the attractancy of the composition. Adjuvants can be evaluated with the compositions of this invention using the attractant-trapant assay regime as provided, for example, in Example III, and as provided in the studies of Examples IV–VI.

In a preferred embodiment, the compositions of this invention are combined with an insect trap to catch insects attracted to the composition. The trap includes any of a variety of means for retaining the fruit flies at or near the trap. Devices for retaining fruit flies include those known in the art such as adhesives, electrocution, toxicants, mazes such as pitfalls, liquids to facilitate drowning, insecticides, and the like and combinations thereof. For example, the composition can be incorporated into a tacky or adhesive matrix and placed on a surface to trap the fruit flies. Fly paper and tacky substances for trapping insects in pheromone traps and the like are known in the art. Preferably, the composition can be incorporated into a sustained release device and placed on or near a trap to retain the flies. Sustained release devices include dispensers that support release of the attractant compositions of this invention over time, preferably for more than about 2 weeks and therefore maintains the ability of the device or dispenser to attract fruit flies for about 2 weeks. A variety of other fly traps and insect traps are known in the art including "bug zappers", trap boxes, including mazes, death traps, fly paper, traps using air to draw insects toward the source, traps that attract with UV light or electromagnetic fields, traps that electrocute, and the like, and those of ordinary skill in the art will be able to readily combine the compositions of this invention with insect traps and with composition release devices, such as sustained released dispensers.

Traps preferably include at least one attractant composition of the present invention and at least one means for retaining the targeted insect. Trapping insects, and in particular fruit flies, is important in packing and grocery facilities where the population of fruit flies, particularly during outbreaks, can be quite large. Similarly in the residential, health care and food-related commercial industries, trapping is important. The traps are preferably able to trap large numbers of fruit flies for fruit processing and handling operations or applications. In other embodiments the traps are preferably pleasant in appearance for use in, for example, residential and certain commercial applications.

In another embodiment of this invention, the compositions are used in combination with a toxicant, such as insecticide. Further, the compositions either alone or in combination with an insecticide can be used as a decoy to draw the flies to a desired site, away from, for example, people, food, or livestock. The composition can be incorporated into any suitable support including a matrix, a wicking device, or a sustained release dispenser, or mixed with an adjuvant serving as an extender or slow-release formulation or as a spreader-sticker.

The invention will now be illustrated by the following non-limiting Examples. All amounts are expressed as parts by weight unless explicitly expressed otherwise.

EXAMPLE I

Preparation of Fruit Fly Attractant Composition

Indole (330 micrograms), or alternatively skatole at a comparable molar concentration, was dissolved in punctilious ethanol (3 milligrams), to form a 1 weight percent solution. The ethanol solution was added to an aqueous solution prepared from mixing sucrose(340 milligrams), glacial acetic acid (67 milligrams), 2-phenylethanol (10 milligrams), and deionized water (1 mL, 0.995 gm). The resulting mixture was used directly in attractant and trapant applications. Alternatively, the resulting mixture could be: stored for future use or reformulation; or further concentrated by evaporation or diluted by dilution with additional water by, for example, from about 0.01 to about 100 times, depending upon the application requirements. When the mixture was stored for future use either neat or more concentrated, or when the mixture was used neat or in a more concentrated form, there was observed by spectroscopic and related analytical methods that the attractant composition additionally contained minor amounts of esterification products, for example, ethyl acetate (EtOAc) and 2-phenyl ethyl acetate (2-PhEtOAc), which compounds are believed to be in situ acid catalyzed esterification products of the corresponding alcohol ingredients and acetic acid. It is noteworthy that attractant formulations augmented by adding additional quantities of either or both the esterification products were comparable or superior to the attractant and trapant properties of the formulations that were emitting only 'fugitive' acetate esters from spontaneous esterification reactions.

In an alternative formulation, when the above fruit fly attractant composition was prepared with trimethylamine substituted in place of the indole or the skatole compound, the trimethylamine compound was freely soluble in water and the ethanol could be added directly to the mixture of other ingredients.

Table 1 shows an exemplary fruit fly attractant-trapant composition and provides an indication of acceptable levels of variability, that is approximate variability ranges, of individual component without substantially compromising the attractant or trapant properties of the composition.

TABLE 1

Attractant bait composition for Drosophila fruit flies.

| Compound | Weight (mg) | Weight Percent (%) | Weight % Variability Range |
|---|---|---|---|
| sucrose | 340 | 23.79 | 10–500 mg |
| acetic acid | 67 | 4.69 | 10–300 mg |
| 2-phenylethanol | 10 | 0.6998 | 0.1–100 mg |
| α-copaene | 5 | 0.3499 | 0.05–50 mg |
| 2-phenylethyl acetate | 4 | 0.2799 | 0.1–100 mg |
| ethyl alcohol | 3 | 0.2099 | 0.1–100 mg |
| trimethylamine-HCl | 0.05 | 0.003499 | 0.005–0.5 mg |
| indole | 0.01 | 0.000700 | 0.001–0.1 mg |
| skatole (3-methylindole) | 0.01 | 0.000700 | 0.001–0.1 mg |
| ethyl acetate | trace | trace | trace |
| water | 1,000 | 69.98 | 1000 mg |
| Total | 1429.07 | 100.00 | 1020.357–2150.7 |

Collection of Fruit Volatiles.

Fermenting strawberry, banana, and mango fruits were collected from local grocery stores. The fruits, about 200–300 grams each, were placed in 500 mL glass jars with Teflon-coated caps. The jars were kept at room temperature for further fermentation.

Headspace collection of volatiles from the three different types of fermenting fruits were obtained by two different methods. The first method, which does not require the use of solvents, collected fermenting fruit volatiles directly from the glass jars by solid phase microextraction (SPME) (Supelco, Inc., Bellefonte, Pa.). The SPME device was equipped with an interchangeable fiber coated with a thickness of 100 microns of polydimethylsiloxane that was contained within a syringe. The fiber was extruded from the syringe and inserted into the headspace of a glass jar containing fermenting fruits for 30 minutes at room temperature of about 25–28° C. The air was provided during the collecting process at a rate of 200 mL/min. Then, the fiber was immediately inserted into the injector port of a GC (HP 5890 gas chromatograph, Hewlett-Packard Co., Palo Alto, Calif.) where it was thermally desorbed (250° C.).

For the second method, the cap of the glass jar containing fermenting fruit was pre-drilled with two holes, and charcoal-filtered air was blown through one hole at a rate of 500 mL/min. Volatiles were collected in a modified glass pipette (10 cm long with a 5 mm interior diameter [RD]) containing 300 mg of pre-cleaned Tenax® TA (Alltech Associated, Inc., Deerfield, Ill.), and the pipette was connected with another hole. The Tenax® TA trap was desorbed with 1 mL of redistilled HPLC-grade hexane. Each sample was concentrated to about 100 microliters under nitrogen and immediately analyzed by GC-EAG and GC-MS.

Chemical analysis.

Two-three microliter aliquots of the Tenax® collected fruit volatiles were injected in spitless mode onto 30 m×0.25 mm ID fused silica capillary gas chromatographic columns, (DB-5, J & W Scientific, Folson, Calif.) for analysis by GC-EAG and GC-MS. Column conditions were as follows: Helium was used as the carrier gas at a flow rate of 30 mL/min, injector temperature 250° C., 1 min delay on inlet purge, 4 min at 50° C. then 10° C. or 15° C./min to 250° C. The SPME collections were analyzed by using the same conditions described above. GC-MS analyses were performed by using the HP 5890 GC with a direct interface to a Hewlett-Packard 5970 mass selective detector (electron impact, 70 eV).

EXAMPLE II
Identification of EAG Active Compounds.

Drosophila melanogaster colonies were maintained at the Department of Entomology, Iowa State University, under the condition of 25° C. temperature and 14:10 (light:dark) photoperiod regime. One to ten days old fruit flies were used for the experiments. Combined GC-EAG analysis were carried out by using a HP-5890 GC. A fine tip glass electrode was inserted in the compound eye, and served as reference electrode. Another fine tip glass electrode was brought into contact with the distal end of the funiculus of an antenna. Both glass electrodes were filled with 1 M KCl solution. More than fifty GC-EAG analyses of the volatiles collected form the fruit samples were obtained. Only those GC peaks that consistently revealed simultaneous EAG activity were targeted for further analysis although similar analyses could be performed on compounds stimulating any EAG activity. GC-EAD analyses consistently revealed twenty-two compounds GC peaks on DB-5 column with corresponding EAG activity on fruit fly antennae. The retention times on the GC column and GC-MS spectra of these compounds corresponded precisely to those known to be present in the fruit volatiles. These compounds were identified and listed in Table 2 along with the measured relative EAG activity response.

TABLE 2

EAG active compounds from fermenting fruit in Drosophila melanogaster antennae.

| Compound | EAG activity |
| --- | --- |
| ethanol | +++ |
| ethyl acetate | ++ |
| butyl acetate | +++ |
| isoamyl acetate | +++ |
| ethyl butanoate | ++ |
| styrene | +++ |
| 2-heptanol | +++ |
| ethyl-2-methyl-2-butenoate | ++ |
| ethyl carproate | ++ |
| 3-hexenyl acetate | + |
| hexyl acetate | + |
| Isobutyl butyrate | + |
| ethyl-2-hexenoate | + |
| ethyl furoate | + |
| 2-methylbutyl-2-methyl butanoate | +++ |
| (Z)-4-hexenyl butanoate | +++ |
| 2-phenyl-2-propanol | + |
| 2-methylbutyl hexanoate | ++ |
| propyl hexanoate | ++ |
| linalool | ++ |
| eugenol | +++ |
| 2-phenylethanol | +++ |
| 1,2-dimethoxy-4-(2-propenyl)-benzene | +++ |
| phenylmethyl acetate | +++ |
| ethyl benzoate | ++ |
| Alpha-terpinolene | + |
| (E)-Caryophyllene | + |
| naphthalene | + |
| ethylphenyl acetate | ++ |
| 2-phenylethyl acetate | ++ |
| ethyl salicylate | + |
| ethyl-3-phenyl-2-propyl acetate | ++ |

EXAMPLE III
Attraction-Trapant Behavioral Bioassays

Three different sizes of screen cages (w×h×l: 26 cm×26 cm×30 cm; 48×61×61; and 88×36×46) were used for the trapping experiments. Trapping experiments were carried out either in the laboratories, or in nearby green houses.

The attraction-trapant assay traps were constructed from cylindrical, clear plastic jelly cups (4.0 cm I.D. at top, 3.0 cm I.D. bottom; 2.5 cm high) with a tightly fitting paper lid. The lids were pre-drilled with a hole having a diameter of about 2 mm, which was the only aperture through which volatiles from candidate attractants could emanate, and also the only entrance through which attracted flies could enter the trap chamber. In all experiments, a 1-cm-long, 0.5-cm-diameter piece of cotton dental wick was used as the substrate onto which different compositions of potential attractants were loaded for testing, and then the wick was placed in the bottom of the cup and the lid then sealed in position at the beginning of testing.

Traps containing a series of compositions to be compared were tested in a randomized, complete-block design, with one replicate of a treatment series deployed per cage. The traps were placed in an array with usually approximately 15 cm between traps. If three treatments were to be compared (including control), the array took the form of a triangle. If there were four treatments, then the four trap-cups formed a square.

No glue or toxicant was used inside the traps, and captures depended on the ability of the attractant-trapant composition to both attract the fruit flies as well as retain them in the chamber by keeping them from wandering back to the entrance hole on the lid and exiting through it. During these assays, observations of the fruit flies' behavior were often made, and they could routinely be observed flying slowly around the cage before descending to one of the traps on the floor of the cage, landing on it, and then walking more or less directly to the hole on the lid and entering the trap. Many times newly-arrived flies were observed to repeatedly enter and exit the hole after first being attracted to it, before finally disappearing through the hole into the trap for a much longer period.

For each experiment between 200–300 fruit flies of Drosophila melanogaster adult fruit flies of both sexes were released into a cage directly from their rearing bottles that contained fruit fly artificial larval rearing medium. The numbers of flies within the traps were counted after a predetermined period for each experiment; usually 8 hours. During this period the trap positions were rotated at several hour intervals in order to minimize any possible trap position effects.

These attraction-trapant assays were used to assess the attractant-trapant activity of the identified neurophysiologically active fruit volatiles and permitted testing of various other compositions and optimization of the compositions by testing a variety of ratios of the compounds forming the compositions of this invention.

EXAMPLE IV

The attraction-trapant assays early-on identified at least two mixtures of synthetic components based on some of the compounds indicated from headspace volatile analysis plus GC-EAG results, to be potentially behaviorally active. One composition comprised seven compounds: 2-phenyl ethanol; benzyl acetate; ethyl benzoate; 2-phenylethyl acetate; ethyl phenylacetate; ethyl salicylate; and ethyl cinnamate, see Table 3. The trapant-attractancy of any one individual EAG-active compound tested was not much greater than that of the control; however, the combined effect of the components as a composition generated highly significant attractant-trapant activity.

TABLE 3

Comparison of Drosophila fruit fly capture numbers in cup traps with different volatile compounds or mixtures identified from fermenting fruit.

| Compound (mg) | Catches per day (mean ± S.E.) |
|---|---|
| 2-Phenylethanol (1 mg) | 0.5 ± 0.29 |
| 2-Phenylethanol (5 mg) | 1.25 ± 0.63 |
| 2-Phenylethanol (10 mg) | 3.15 ± 1.63 |
| Benzyl acetate (10 mg) | 0.5 ± 0.27 |
| Ethyl benzoate (10 mg) | 0.25 ± 0.16 |
| Ethyl phenylacetate (10 mg) | 1.5 ± 0.5 |
| 2-Phenylethyl acetate (10 mg) | 1.87 ± 0.81 |
| Ethyl salicylate (10 mg) | 0.37 ± 0.18 |
| Ethyl cinnamate (10 mg) | 0.75 ± 0.49 |
| 7-Component blend (10 mg) | 6.25 ± 2.01 |
| Malt extract (10 mg) | 1.02 ± 0.46 |
| Control | 0.037 ± 0.18 |

Solvent (dichloride methane) was used as control. 100–150 flies were released in the cage, traps were checked daily for 5 days.

A second composition comprising only acetic acid and 2-phenyl ethanol was also found in early studies to be a composition capable of attracting and trapping fruit flies, see Table 4. The ratio of acetic acid to the 2-phenylethanol was found to be important to the optimization of the attraction-trapant activity.

TABLE 4

Comparison of the number of Drosophila fruit flies retained in traps using different ratios of acetic acid and 2-phenylethanol.

| Acetic acid | 2-Phenylethanol | Catches per day (Mean ± S.E.) |
|---|---|---|
| 100 | 0 | 3.0 ± 1.08 |
| 90 | 10 | 19.5 ± 13.6 |
| 70 | 30 | 9.75 ± 3.04 |
| 50 | 50 | 7.75 ± 1.8 |
| 30 | 70 | 6.0 ± 2.94 |
| 10 | 90 | 6.75 ± 4.02 |
| 0 | 100 | 0 ± 0 |
| 0 | 0 | 0 ± 0 |

The total amount of each lure was 10 mg, and solvent used as control. No water was added. 100–150 flies were released in the cage, traps were checked daily for 5 days.

Further experiments showed that such blends could be solubilized in a sucrose-water solution, and that the resulting aqueous solution increased the trapant-attractancy significantly, see Table 5.

TABLE 5

Effect of sucrose-water solution on Drosophila trap catches.

| Bait | Trap catches | Replicates |
|---|---|---|
| Acetic acid + 2-phenyl ethanol | 1.38 ± 0.65 | 8 |
| Acetic acid + 2-phenyl ethanol + Sucrose + H$_2$O | 19.13 ± 5.72 | 8 |
| Blank Control | 0 | 8 |

In a further experiment increased attraction-trapant activity was shown to be attributable to the presence of both water and the sugar. The attractant composition plus water and sucrose captured more fruit flies than the attractant composition solubilized in water alone as shown in Table 6.

TABLE 6

Effect of water and sucrose-water on Drosophila trap catches.

| Bait | Trap catches | Replicates |
|---|---|---|
| Acetic acid + 2-phenyl ethanol + H$_2$O | 93.88 ± 22.62 | 8 |
| Acetic acid + 2-phenyl ethanol + H$_2$O + sucrose | 135.75 ± 27.16 | 8 |
| Blank Control | 0 | 8 |

The importance of 2-phenyl ethanol to trapant-attractancy was again shown in an experiment using a blend of 67 parts acetic acid, 10 parts 2-phenyl ethanol, 3 parts ethanol, 500 parts sucrose, and 1,000 parts water. For example, 1 mL of this solution was placed on the cotton wick in a cup trap. A second blend identical to the above blend with the exception that the 2-phenyl ethanol was omitted was used as a second composition. The number of fruit flies captured in the trap was significantly reduced using the second composition, see Table 7.

TABLE 7

Effect of 2-phenyl ethanol on Drosophila trapant-attractancy.

| Bait | Trap catches | Replicates |
|---|---|---|
| Acetic acid + 2-phenyl ethanol + H$_2$O + sucrose + 2-phenyl ethanol | 92.00 ± 16.81 | 6 |
| Acetic acid + 2-phenyl ethanol + H$_2$O + sucrose | 44.67 ± 17.20 | 6 |
| Blank Control | 0 | 6 |

The above blend containing acetic acid, ethanol, 2-phenyl ethanol, and sucrose in water was further enhanced in trapant-attraction by the addition of small amounts of either the nitrogen heterocycles, indole and skatole, or the trialkyl amine salt, trimethylamine HCl. Table 8 shows the increased capture of fruit flies when indole is added to the blend. Table 9 shows the increased trapant-attraction when skatole is added. Table 10 illustrates that trimethylamine HCl admixed with the blend also increases trapant-attractancy.

TABLE 8

Effect of adding indole to the composition.

| Bait | Trap catches | Replicates |
|---|---|---|
| Acetic acid + ethanol + H$_2$O + sucrose + 2-phenyl ethanol | 49.17 ± 13.88 | 6 |
| Acetic acid + ethanol + H$_2$O + sucrose + 2-phenyl ethanol + indole | 70.17 ± 10.22 | 6 |
| control blank | 0 | 6 |

TABLE 9

Effect of adding skatole to the composition.

| Bait | Trap catches | Replicates |
|---|---|---|
| Acetic acid + ethanol + H$_2$O + sucrose + 2-phenyl ethanol | 67.67 ± 13.64 | 6 |
| Acetic acid + ethanol + H$_2$O + sucrose + 2-phenyl ethanol + skatole | 94.50 ± 26.31 | 6 |
| control blank | 0 | 6 |

TABLE 10

Effect of adding trimethylamine HCl to the composition.

| Bait | Trap catches | Replicates |
|---|---|---|
| Acetic acid + ethanol + H$_2$O + sucrose + 2-phenyl ethanol | 57.67 ± 12.13 | 6 |
| Acetic acid + ethanol + H$_2$O + sucrose + 2-phenyl ethanol + trimethylamine-HCl | 71.00 ± 8.40 | 6 |
| control blank | 0 | 6 |

In addition, it was found that the ratio of indole in the composition can affect attraction-trapant activity. Table 11 data illustrated that lower, as opposed to higher, proportions of indole in the composition create greater attraction-trapant activity.

TABLE 11

Effects of indole dosages on fruit fly catches.

| Indole in composition* (mg) | No. fruit flies per trap (mean ± S.E.) (N = 9) |
|---|---|
| 0.01 | 67 ± 13 |
| 0.3 | 77 ± 24 |
| 3 | 14 ± 4 |
| 30 | 27 ± 10 |

*Composition consists of 3 mg of ethanol, 67 mg of acetic acid, 10 mg of 2-phenylethanol, and 340 mg of sucrose in 1 mL water.

The invention also provides for the addition of other various synthetic volatile components which can mimic compounds emanating from natural sources and which compounds are also attractive to Drosophila fruit flies. The additional components can further enhance the attraction-trapant activity of the composition, such as those that were isolated and identified from the headspace analysis of ripe or decaying fruit, see for example, Example II above. Table 12 illustrates that the addition of a terpenoid compound, such as alpha-copaene, to the composition increased the compositions attraction-trapant activity.

TABLE 12

Effect of adding alpha-copaene to the composition.

| Bait | Trap catches | Replicates |
|---|---|---|
| Acetic acid + ethanol + H$_2$O + sucrose + 2-phenyl ethanol | 59.83 ± 10.51 | 6 |
| Acetic acid + ethanol + H$_2$O + sucrose + 2-phenyl ethanol + alpha-copaene | 77.83 ± 25.73 | 6 |
| control blank | 0 | 6 |

The invention also provides for fugitive compounds that are spontaneously generated in situ by esterification reactions between alcohols and acids in the composition and are present in the airborne collections of volatiles emanating from the source. The fugitive compounds can also enhance attraction-trapant activity. This was explored by preparing various attractant-trapant blends that were augmented with additional amounts of candidate fugitive ester compounds. Tables 13 and 14 data showed that adding ethyl acetate to a composition increased the attraction-trapant activity of the composition. Table 15 data illustrated that increased attraction-trapant activity results from augmenting a composition with additional 2-phenylethylacetate.

TABLE 13

Effect of ethyl acetate on attraction-trapant activity.

| Bait | Trap catches | Replicates |
|---|---|---|
| Acetic acid | 0.25 ± 0.16 | 8 |
| Acetic acid + ethyl acetate | 2.63 ± 1.15 | 8 |
| Blank Control | 0 | 8 |

TABLE 14

Effect of ethyl acetate on attraction-trapant activity.

| Bait | Trap catches | Replicates |
|---|---|---|
| Acetic acid + 2-phenyl ethanol | 1.38 ± 0.65 | 8 |
| Acetic acid + 2-phenylethanol + ethyl acetate | 2.63 ± 1.15 | 8 |
| Blank Control | 0 | 8 |

TABLE 15

Effect of 2-phenylethyl acetate on attraction-trapant activity.

| Bait | Trap catches | Replicates |
|---|---|---|
| Acetic acid + 2-phenyl ethanol | 15.50 ± 0.50 | 2 |
| Acetic acid + ethyl acetate | 22.00 ± 10.00 | 2 |
| Blank Control | 0 | 2 |

In all of the trapping experiments, both male and female fruit flies were trapped in equivalent numbers similar to the ratio trapped in response to ripe mango fruit, illustrating that these compositions are general feeding and oviposition attractants and are not related to sex pheromones, as illustrated in Table 16.

TABLE 16

Sex ratios of flies captured in response to various compositions.

| | Trap catches | | # of traps |
|---|---|---|---|
| Bait* | Males | Females | examined |
| Blend 1 | 17 | 24 | 3 |
| Blend 2 | 141 | 155 | 7 |
| 1 gm Ripe Mango Fruit | 10 | 6 | 10 |

*Blend 1 consists of 200 mg of acetic acid, 10 mg of 2-phenylethanol, and 200 mg of sucrose in 400 mL water.
*Blend 2 consists of 3 mg of ethanol, 67 mg of acetic acid, 10 mg of 2-phenylethanol, 0.01 mg indole, and 340 mg of sucrose in 1 mL water.

In addition, the captured fruit flies themselves did not emit additional volatile attractants that influenced the capture, as illustrated in Table 17, which shows that live fruit flies experimentally placed in traps containing sucrose-water do not result in greater attraction-trapant activity than does the sucrose-water alone.

TABLE 17

Attractiveness of live fruit flies.

| Bait | Trap catches | Replicates |
|---|---|---|
| 50 Live fruit flies | 2.33 ± 0.99 | 9 |
| Sugar water | 2.33 ± 0.55 | 9 |
| Control | 0 | 3 |

The attraction-trapant activity of the synthetic blends were greater than the natural ripe fruit sources from which the analyses of volatiles were performed, as illustrated in Table 18 in which the synthetic blend was emitted from one set of traps and 1 gram of sliced, ripe mango fruit was placed in another set of traps. Furthermore, the synthetic blends were able to attract and trap Drosophila fruit flies even in the presence of ripe mango fruit placed within the assay cage only tens of centimeters from the cup traps containing the synthetic blends, as illustrated in Table 19.

TABLE 18

Comparison of attractiveness between synthetic bait and mango fruit for fruit fly.

| Bait | Trap catches | Replicates |
|---|---|---|
| Synthetic Composition* | 50.00 ± 7.62 | 12 |
| 1 g Ripe Mango Fruit | 5.92 ± 1.21 | 12 |
| Blank Control | 0 | 4 |

*Synthetic composition consists of 3 mg of ethanol, 67 mg of acetic acid, 10 mg of 2-phenylethanol, 0.01 mg indole, and 340 mg of sucrose in 1 mL water.

TABLE 19

Comparison of attractiveness between synthetic bait and mango fruit for fruit fly when mango fruits were present nearby.

| Bait | Trap catches | Replicates |
|---|---|---|
| Synthetic bait* (JW) | 26.17 ± 6.05 | 6 |
| Mango fruit* | 1.00 ± 0.52 | 6 |
| Control | 0 | 2 |

*Two ripened mango fruits were placed on the floors of the cages where the cup traps were located.

EXAMPLE V

The fruit fly attractant and trapant compositions of the present invention were tested against the aforementioned "Natural Catch® Plus Fruit Fly Trap" commercial product believed to be disclosed in the above U.S. Pat. No. 5,490,349.

The attractant and trapant compositions of the present invention consistently and routinely performed better than the unknown attractant material contained in the "Natural Catch® Plus Fruit Fly Trap". As illustrated in Table 20, there was observed substantially greater "capture" or "catches", that is, fruit fly trap levels, with the attractant-trapant compositions of the present invention contained in a crude cup type traps compared side-to-side to the liquid solution that serves as the attractant in the Natural Catch® product.

TABLE 20

Comparison of attractiveness between synthetic baits and a commercial attractant bait.

| Experiment | Bait | Trap catches | Replicates |
|---|---|---|---|
| I | Blend 1 | 19.13 ± 5.72 | 8 |
|   | Anderson's Solution | 8.75 ± 2.91 | 8 |
|   | control | 0 | 8 |
| II | Blend 1 | 25.42 ± 2.49 | 19 |
|   | Anderson's Solution | 22.68 ± 1.83 | 19 |
|   | control | 0 | 2 |
| III | Blend 2 | 26.50 ± 1.50 | 2 |
|   | Anderson's Solution | 8.50 ± 0.50 | 2 |
| IV | Blend 1 | 9.10 ± 1.76 | 20 |
|   | Anderson's Solution | 3.05 ± 0.92 | 19 |

TABLE 20-continued

Comparison of attractiveness between synthetic baits and a commercial attractant bait.

| Experiment | Bait | Trap catches | Replicates |
|---|---|---|---|

*Blend 1 consists of 200 mg of acetic acid, 10 mg of 2-phenylethanol, and 200 mg of sucrose in 400 mL water.
*Blend 2 consists of 3 mg of ethanol, 67 mg of acetic acid, 10 mg of 2-phenylethanol, 0.01 mg indole, and 340 mg of sucrose in 1 mL water.

All publications, patents, and patent documents cited above are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A Drosophila fruit fly attractant composition comprising:
   a volatile short chain carboxylic acid,
   a volatile short chain alcohol,
   a volatile aryl substituted alcohol, and
   a nitrogen compound.

2. The composition of claim 1, further comprising water.

3. A Drosophila fruit fly attractant composition comprising:
   a volatile short chain carboxylic acid,
   a volatile short chain alcohol,
   a volatile aryl substituted alcohol,
   a nitrogen compound, and a sugar.

4. The composition of claim 3, wherein the sugar is sucrose.

5. A Drosophila fruit fly attractant composition comprising:
   a volatile short chain carboxylic acid,
   a volatile short chain alcohol,
   a volatile aryl substituted alcohol,
   a nitrogen compound, and ethylacetate.

6. A Drosophila fruit fly attractant composition comprising:
   a volatile short chain carboxylic acid,
   a volatile short chain alcohol,
   a volatile aryl substituted alcohol,
   a nitrogen compound, and 2-phenylethylacetate.

7. The composition of claim 3, wherein the volatile short chain carboxylic acid is acetic acid, the volatile short chain alcohol is ethanol, the aryl substituted alcohol is 2-phenyl ethanol, and the nitrogen compound is indole.

8. A Drosophila fruit fly attractant composition comprising:
   a volatile short chain carboxylic acid,
   a volatile short chain alcohol,
   a volatile aryl substituted alcohol, and
   a nitrogen compound, wherein the nitrogen compound is indole, 3-methyl-1H-indole, or a trialkyl amine.

9. The composition of claim 8, wherein the trialkylamine is trimethylamine.

10. The composition of claim 1, wherein the volatile short chain carboxylic acid is present in an amount of from about 10 to about 300 weight percent, the volatile short chain alcohol is present in an amount of from about 1 to about 30 weight percent, the volatile aryl substituted alcohol is present in an amount of from about 0.1 to about 100 weight percent, and the nitrogen compound is present in an amount of from about 0.001 to about 1.0 weight percent.

11. The composition of claim 10, further comprising from about 10 to about 1,000 weight percent sucrose, and from about 10 to about 1,000 weight percent water.

12. A Drosophila fruit fly attractant-trapant composition comprising:
   from about 30 to about 100 weight percent acetic acid,
   from about 1 to about 10 weight percent ethanol,
   from about 1.0 to about 30 weight percent 2-phenyl ethanol, and
   from about 0.01 to about 1.0 weight percent of a nitrogen compound.

13. The composition of claim 12, further comprising from about 200 to about 500 weight percent sucrose, and from about 100 to about 10,000 weight percent water.

14. The composition of claim 12, further comprising from about 0.3 to about 3 weight percent of ethylacetate, and from about 0.3 to about 10 weight percent of 2-phenylethylacetate.

15. The composition of claim 12, wherein the nitrogen compound is indole, 3-methyl-1H-indole, or a trialkylamine or a salt thereof with from 3 to about 12 carbon atoms, and mixtures thereof.

16. The composition of claim 15, wherein the trialkylamine compound is trimethylamine.

17. The composition of claim 15, wherein the trialkylamine compound is triethylamine.

18. The composition of claim 12, further comprising an insecticide.

19. The composition of claim 12, contained in a sustained release dispenser.

20. A Drosophila fruit fly attractant-trapant composition comprising:
   from about 65 to about 70 weight percent acetic acid,
   from about 2 to about 4 weight percent ethanol,
   from about 9 to about 11 weight percent 2-phenyl ethanol,
   from about 0.01 to about 0.5 weight percent of a nitrogen compound,
   from about 10 to about 1,000 weight percent a sugar, and
   from about 10 to about 1,000 weight percent water.

21. The composition of claim 20, wherein the nitrogen compound is indole, skatole, or trimethylamine.

22. The composition of claim 20, wherein the sugar is sucrose.

23. The composition of claim 20, wherein the sugar is sucrose, glucose, fructose, or mixtures thereof.

24. A synthetic Drosophila fruit fly attractant composition prepared by combining: acetic acid, ethanol, 2-phenyl ethanol, and a nitrogen compound of indole, skatole, trimethylamine, or mixtures thereof.

25. The composition of claim 24, further comprising sucrose, glucose, fructose, water, 2-phenyl ethyl acetate, ethyl acetate, or mixtures thereof.

26. A kit useful for attracting and trapping Drosophila fruit flies comprising:
   a bait in accordance with the composition of claim 1 in an amount effective to attract Drosophila fruit flies, and
   a housing adapted for containing the bait and for retaining the attracted Drosophila fruit flies.

27. A Drosophila fruit fly trap comprising a housing to retain fruit flies within the trap and the synthetic fruit fly attractant-trapant composition of claim 20.

28. The trap of claim 27, wherein the housing includes a tacky surface, an insecticide, a pheromone, a trap box, an electrocution means, a liquid reservoir, a heat stimuli, a visual stimuli, or combinations thereof.

29. A method for attracting Drosophila fruit flies comprising:
   positioning in a fruit fly area an effective amount of a Drosophila fruit fly attracting composition comprising:
      from about 10 to about 300 weight percent acetic acid,
      from about 1 to about 30 weight percent ethanol, and
      from about 0.1 to about 100 weight percent 2-phenyl ethanol,
      from about 0.001 to about 1.0 weight percent of a nitrogen compound,
      from about 10 to about 1,000 weight percent of a sugar, and
      from about 10 to about 1,000 weight percent water.

30. The method of claim 29, wherein the composition stimulates a volatile plume-oriented upwind flight of a Drosophila fruit fly in a wind tunnel having a wind velocity of about 50 cm/second.

31. The method of claim 29, wherein the composition stimulates an electroantennogram response from a Drosophila fruit fly antenna.

32. The method of claim 29, further comprising incorporating the composition as part of a trap for collecting the attracted flies.

33. The method of claim 29, wherein the fruit fly area includes fresh, frozen, or processed, fruit or produce.

34. The method of claim 29, wherein the Drosophila fruit fly is *Drosophila melanogaster*.

35. The method of claim 29, wherein the Drosophila fruit fly attracting composition further comprises from about 0.3 to about 3 weight percent of ethylacetate, and from about 0.3 to about 10 weight percent of 2-phenylethylacetate.

36. A Drosophila fruit fly attractant composition prepared by combining a simple sugar; a volatile carboxylic acid; a short alkyl chain alcohol; an aryl substituted short alkyl chain alcohol; and at least one nitrogen heterocycle compound to provide the composition which attracts a substantial majority of available Drosophila fruit flies and in preference to decaying fruit or produce situated in close proximity to the attractant composition.

37. A Drosophila fruit fly attractant composition comprising:
   a volatile short chain carboxylic acid,
   a volatile short chain alcohol,
   a volatile aryl substituted alcohol,
   a nitrogen compound, and a terpene compound.

38. The composition in accordance with claim 37, wherein the terpene compound is alpha-copaene, alpha-pinene, beta-pinene, beta-myrcene, alpha-terpinene, linalool, carene, trans-beta-caryophyllene, limonene, beta-selinene, or mixtures thereof.

39. The composition in accordance with claim 37, wherein the terpene compound is alpha-copaene present in an amount of from about 0.1 to about 10 percent by weight of the total composition.

* * * * *